United States Patent
Perner et al.

(10) Patent No.: US 6,770,040 B2
(45) Date of Patent: Aug. 3, 2004

(54) REHABILITATION DEVICE FOR PERSONS WITH PARESIS OF LOWER LIMBS ENABLING THEM TO WALK

(76) Inventors: Barbara Perner, ul. Daleka 8, PL-02-024 Warszawa (PL); Grzegorz Kordyl, Bedon Nowy, ul. Okrezna 5, PL-95-020 Andrespol (PL); Michal Kenner, ul. Kochanowskiego 9 m 12, PL-91-459 Lodz (PL)

( * ) Notice: Subject to any disclaimer, the term of this patent is extended or adjusted under 35 U.S.C. 154(b) by 179 days.

(21) Appl. No.: 10/182,266

(22) PCT Filed: May 21, 2001

(86) PCT No.: PCT/PL01/00046
§ 371 (c)(1),
(2), (4) Date: Jul. 25, 2002

(87) PCT Pub. No.: WO01/91675
PCT Pub. Date: Dec. 6, 2001

(65) Prior Publication Data
US 2003/0004444 A1 Jan. 2, 2003

(30) Foreign Application Priority Data
May 30, 2000 (PL) .................................. 340440
Apr. 27, 2001 (PL) .................................. 347347

(51) Int. Cl.$^7$ ................................................ A61H 3/00
(52) U.S. Cl. ................. 601/5; 601/35; 602/23; 482/124

(58) Field of Search ................. 601/5, 23, 34, 601/35; 602/23; 482/74–76, 124, 56, 69; 434/255; 623/24, 30, 31, 28

(56) References Cited

U.S. PATENT DOCUMENTS

| | | | | |
|---|---|---|---|---|
| 2,210,269 A | * | 8/1940 | Taylor | 601/33 |
| 3,358,678 A | * | 12/1967 | Kultsar | 601/23 |
| 4,296,761 A | * | 10/1981 | Tyo | 602/16 |
| 4,566,440 A | * | 1/1986 | Berner et al. | 601/34 |
| 6,666,796 B1 | * | 12/2003 | MacCready, Jr. | 482/51 |
| 6,689,075 B2 | * | 2/2004 | West | 601/23 |

FOREIGN PATENT DOCUMENTS

| | | | |
|---|---|---|---|
| EP | 0237395 | * | 9/1987 |
| GB | 1188647 | * | 4/1970 |
| GB | 2291362 | * | 1/1996 |
| PL | P-319821 | | 11/1998 |
| PL | P-337403 | | 7/2001 |
| WO | WO 90/11742 | * | 10/1990 |
| WO | WO 98/49991 | * | 11/1998 |

* cited by examiner

Primary Examiner—Danton D. DeMille
(74) Attorney, Agent, or Firm—Stites & Harbison PLLC; Marvin Petry

(57) ABSTRACT

Rehabilitation device for persons with paresis of lower limbs enabling them to walk, comprising rocking elements having at their lower part foot elements with platforms for user's feet, said rocking elements being connected, at their upper part by a frame constituting a jacket.

8 Claims, 10 Drawing Sheets

REHABILITATION DEVICE FOR PERSONS WITH PARESIS OF LOWER LIMBS ENABLING THEM TO WALK

The object of this invention is a rehabilitation device for persons with paresis of lower limbs, enabling them to walk.

There are known devices which facilitate handicapped persons to walk; one of these devices being described in Polish patent No 176092, consisting essentially of two parallel flat, quadric mechanisms, situated symmetrically in relation to the vertical axis of the user, the axis of pivotal movement of the symmetrical support elements passing through pelvis joints of the user, where the quadric mechanisms are interconnected by a leading, non-planar quadric mechanism with four elements. the pivot joints of which having axis intersecting in the middle of respective pelvis joint of the user.

In the course of exploitation of the described above rehabilitation device enabling persons with paresis of lower limbs to walk and keep their balance it appeared that its utility value can be noticeably increased and its maneuvering can be facilitated.

Rehabilitation device for persons with paresis of lower limbs enabling them to walk, according to present invention consists essentially of rocking elements having at their lower part foot elements with platforms for user's feet, said rocking elements are connected, at their upper part by a frame constituting a jacket, is characterized by he fact, that it has two basic and two auxiliary rocking elements, where the basic elements consist of two pairs of members, the upper pair and the lower pair of members, where the members of each pair are connected to each other by means of a pivot joint, while the auxiliary rocking elements consist of one pair of members, each member of the pair connected at their lower portion by means of a pivot joint to connectors, which are connected in turn to upper members of basic rocking elements, which are connected, at their lower portion, to foot elements with foot platforms, where, at the uppermost portion of basic and auxiliary rocking elements are connected, by means of pivot joints to angular connectors having bolts rotatably mounted in clasps, slidably mounted on the jacket frame, and where the auxiliary rocking elements are connected, at their lower portion to pistons of spring, gas or hydraulic shock absorbers or to pneumatic or hydraulic cylinders, acting as servomotors, which, at their other ends are pivotally connected to said foot elements, at a distance from connecting pivots of basic rocking elements. Said foot elements consist each of a trapezoidal frame with two pairs of arms, the first pair of arms being parallel to the axis of the person's movement, i.e. axis of symmetry of the device, and the second pair of arms having supports being able to extend outwardly in relation to the axis of symmetry of the device, and where the one, longer arm of the first pair having pivotal joints for the basic rocking elements and shock absorbers, and the second, shorter arm having a foot platform secured thereto. The said foot elements each, having flexible pads underneath, situated, one just under the foot platform and the two other at the ends of outwardly extending arms and where the latter pads being slightly lower than the former ones. The auxiliary rocking elements are interconnected by means of horizontal bipartite interconnections, to which is fixed a plate constituting a seat, in a manner that the basic and auxiliary rocking elements constitute symmetrical left hand and right hand side of the device.

In another embodiment of the invention of the rehabilitation device for persons with paresis of lower limbs, the device is equipped with foot elements having each, a section of channel bar, situated in the middle part of longer trapezium arm, fixed pivotally on a bolt to said longer trapezium arm, and having drilled holes, where, to said bar is attached a bracket with sliding arm, and where at either side of said bolt which pivotally fixes said channel bar are rigidly fixed to the foot element longer arm, two screw bolts with internally threaded bushes there on, having flanges at their lower part, and passing loosely through said drilled holes in said channel bars, and secured outside by clamp nuts, where, in space between bottom of said channel bars and the flanges of said threaded bushes are situated a washer rings made of an elastic material. To each of sliding claps situated on the jacket frame is pivotally attached a channel bar grip, to the wall of which is fixed a bolt with a rotary square plate there on, to which, adjacent at its opposite corners, are rigidly fixed two bolts, to one of which is pivotally attached end of one basic rocking element, to the other, is pivotally fixed the end of one auxiliary rocking element, where to the upper portion of said basic rocking elements are attached handles for person's hand, where the handles are equipped with levers and flexible connectors acting upon locking mechanisms situated on said shock absorbers or servomotors. Each of said square plates has attached at its upper rear part, a connector to which is mounted a shock absorber made of an elastic material, with a screw rod secured into a threaded hole of a bolt, fixed pivotally in a connecting member, fixed solidly to the lower part of said square plate. To the underneath part of said seat there are attached two tubes spaced apart, with two shafts inserted into them, equipped at their respective ends with shock absorbers, made of elastic material, attached by means of additional rods to auxiliary rocking elements.

The described device prove to be more dynamic, more mobile and flexible, which facilitates walking action, and owing to locking mechanisms, connected by means of elastic connectors to handles for person's hands, makes it possible to change the position of the person, from upright standing position to sitting position through many intermediary positions, where the flexible mounting of the seat plate facilitates stepping movement of the person.

Preferred embodiments of the invention will be now described with reference to the accompanying drawings, in which.

Figure 1:
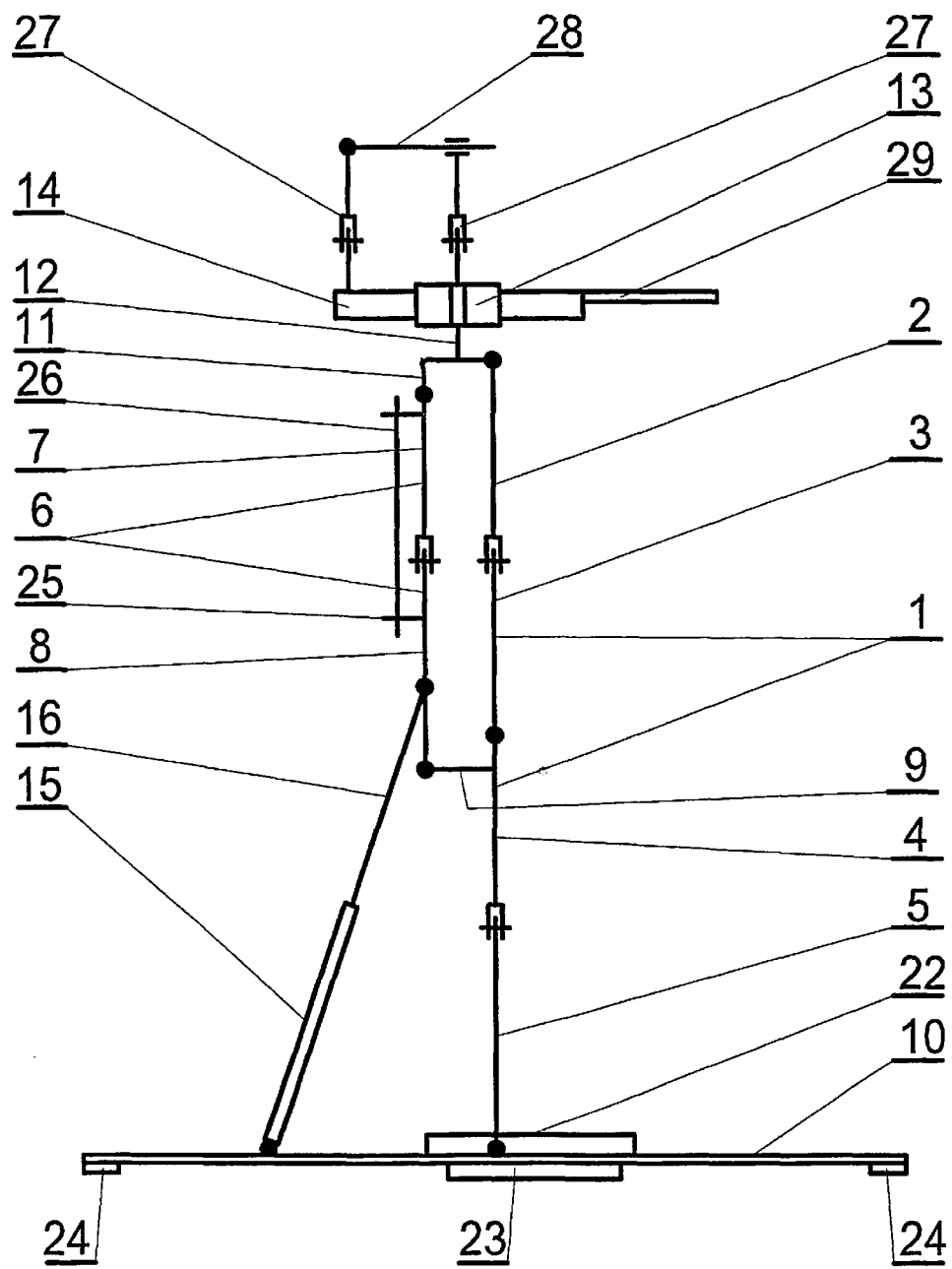
FIG. 1 shows lateral view of he device, drawn in convention of cinematic scheme, when the device is in its upright position.
Figure 2:
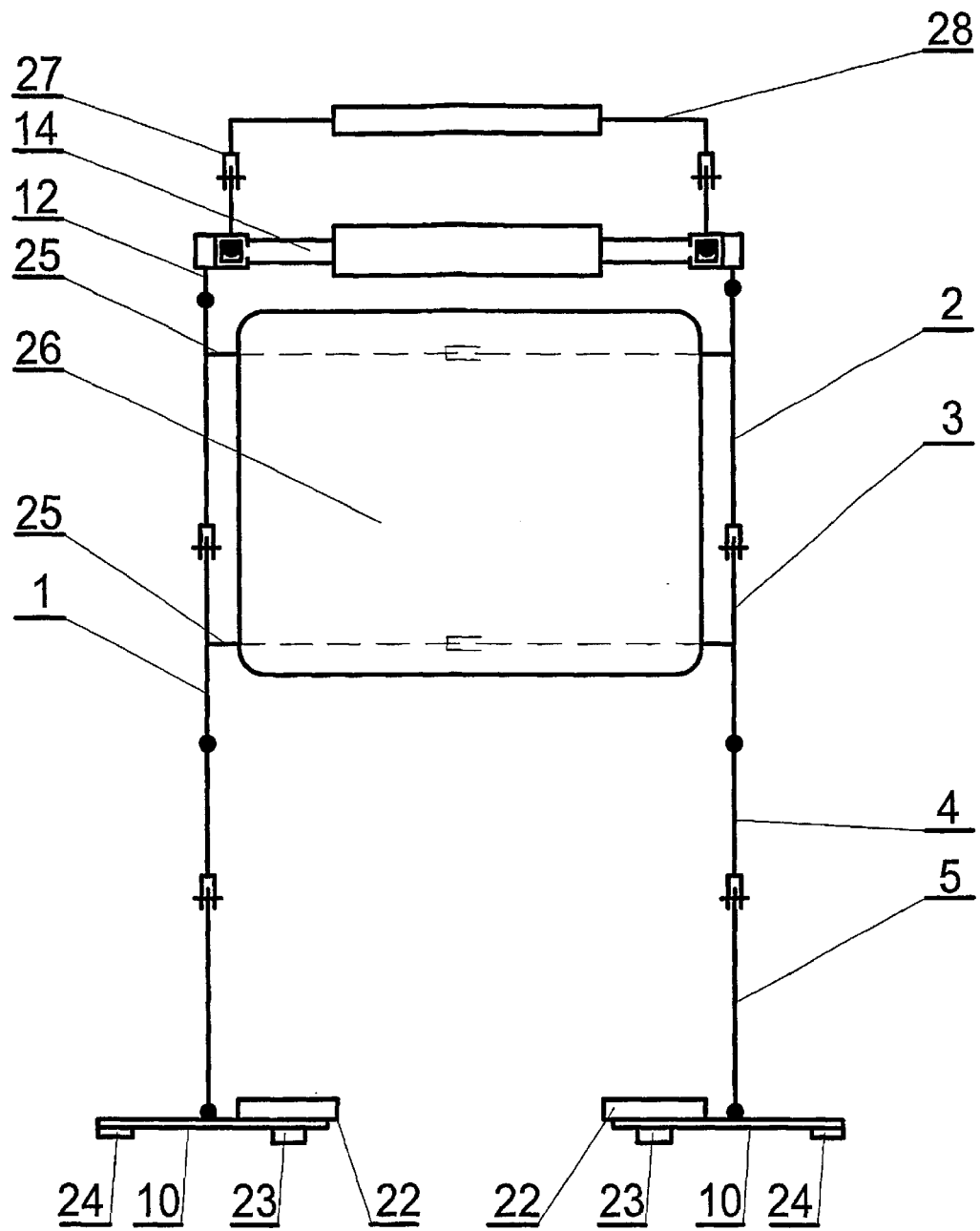
FIG. 2 shows front view of the device, drawn in convention of cinematic scheme, when the device is in its upright position.
Figure 3:
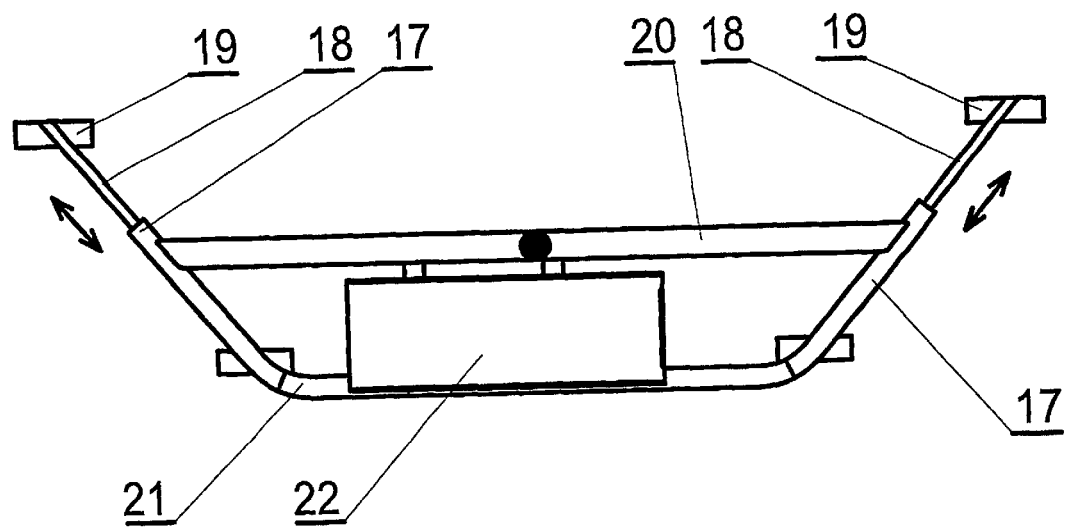
FIG. 3 shows the foot element viewed from above.
Figure 4:
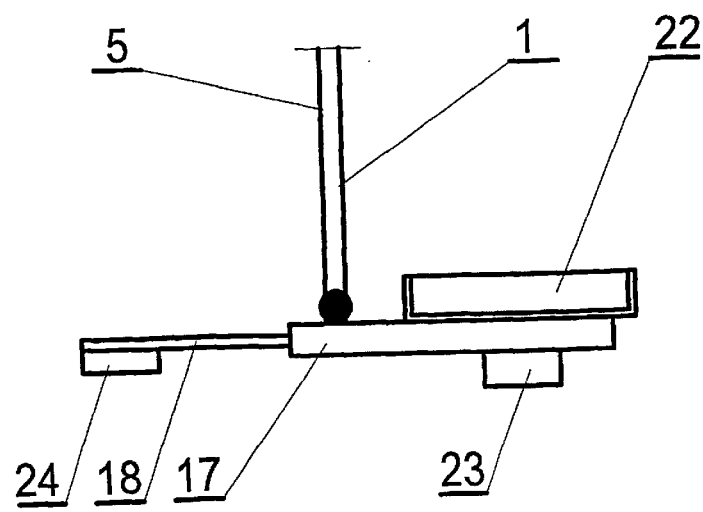
FIG. 4 shows the foot element viewed from the front.
Figure 5:
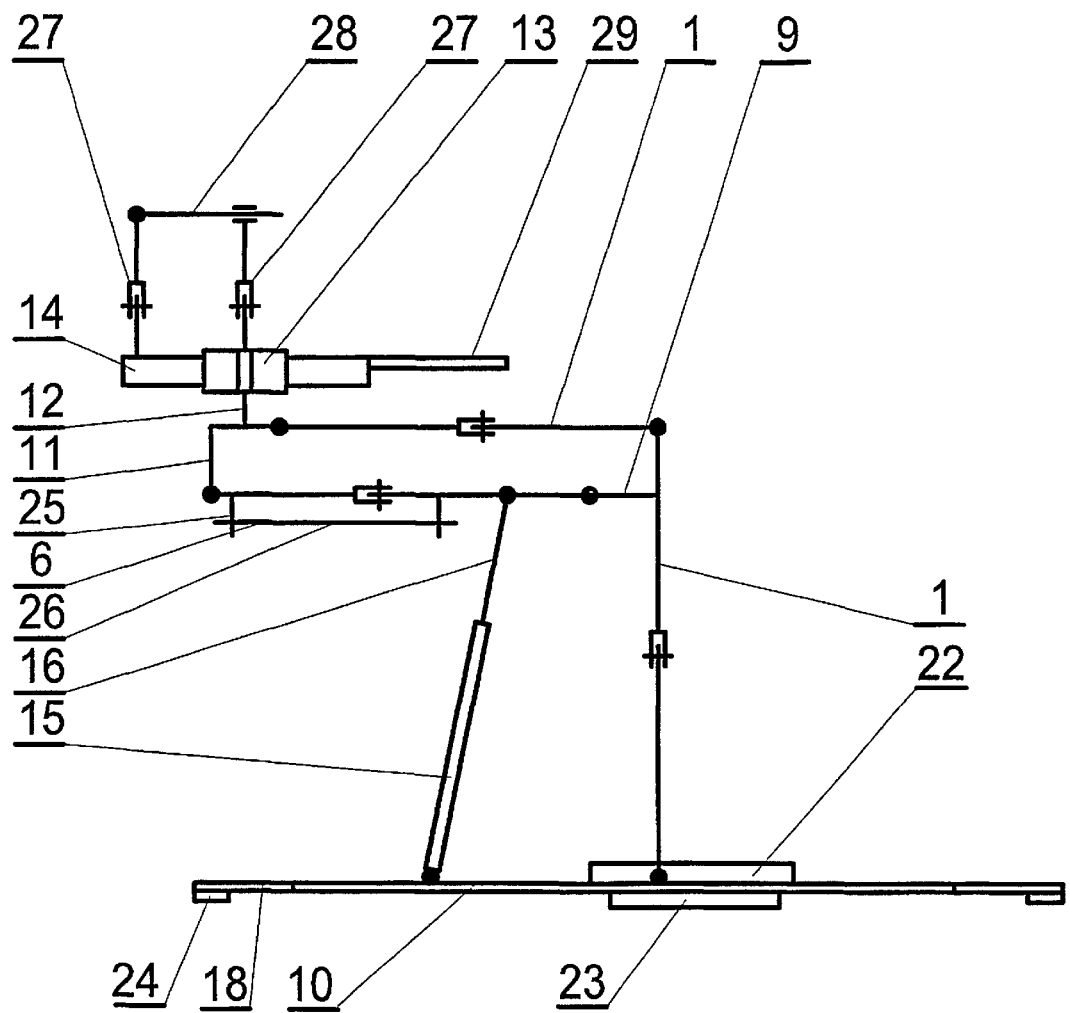
FIG. 5 shows lateral view of the device, drawn in convention of cinematic scheme, when the device is in its seating position.
Figure 6:
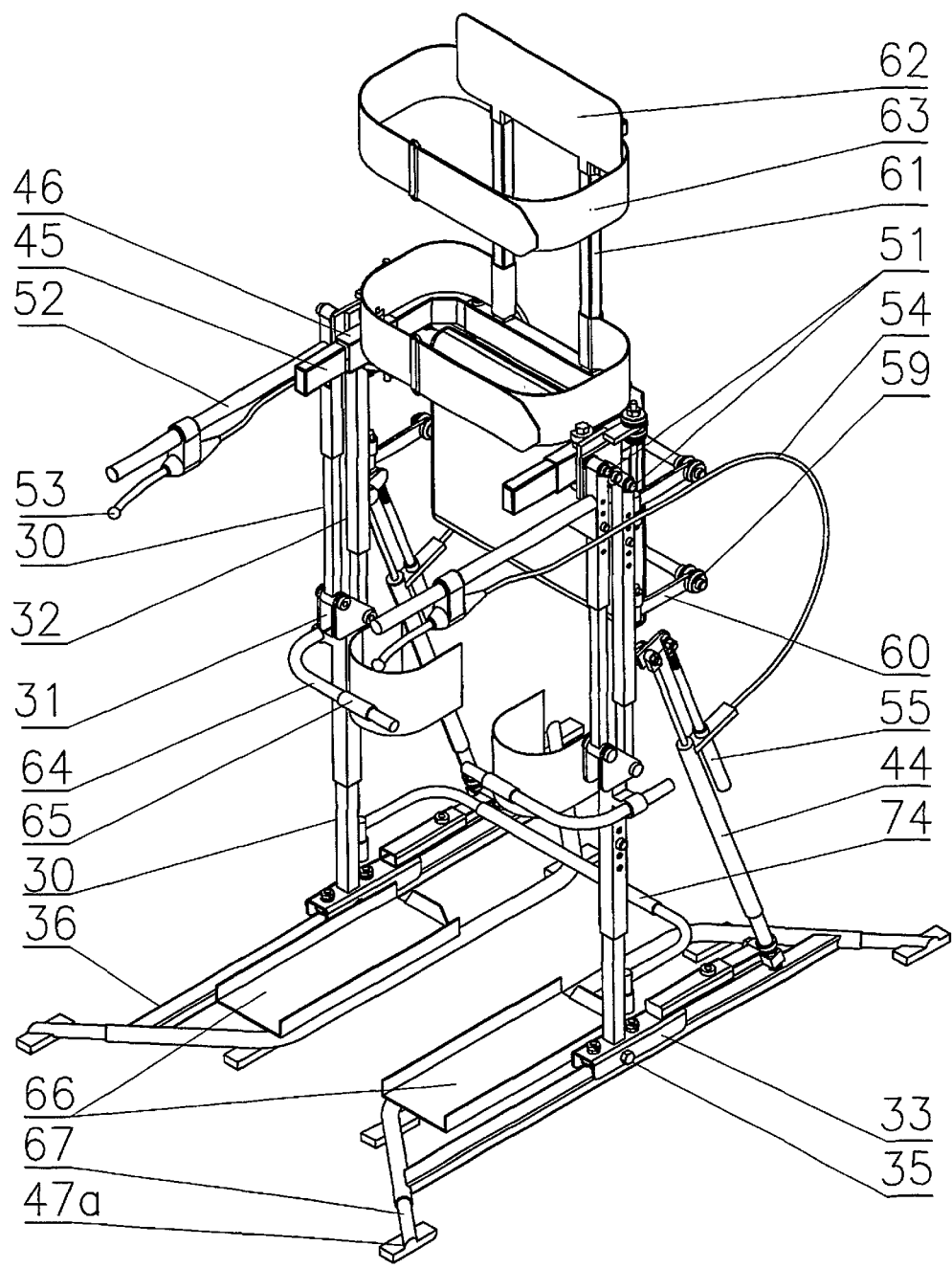
FIG. 6 is a perspective view of the device, seeing from the front.
Figure 7:
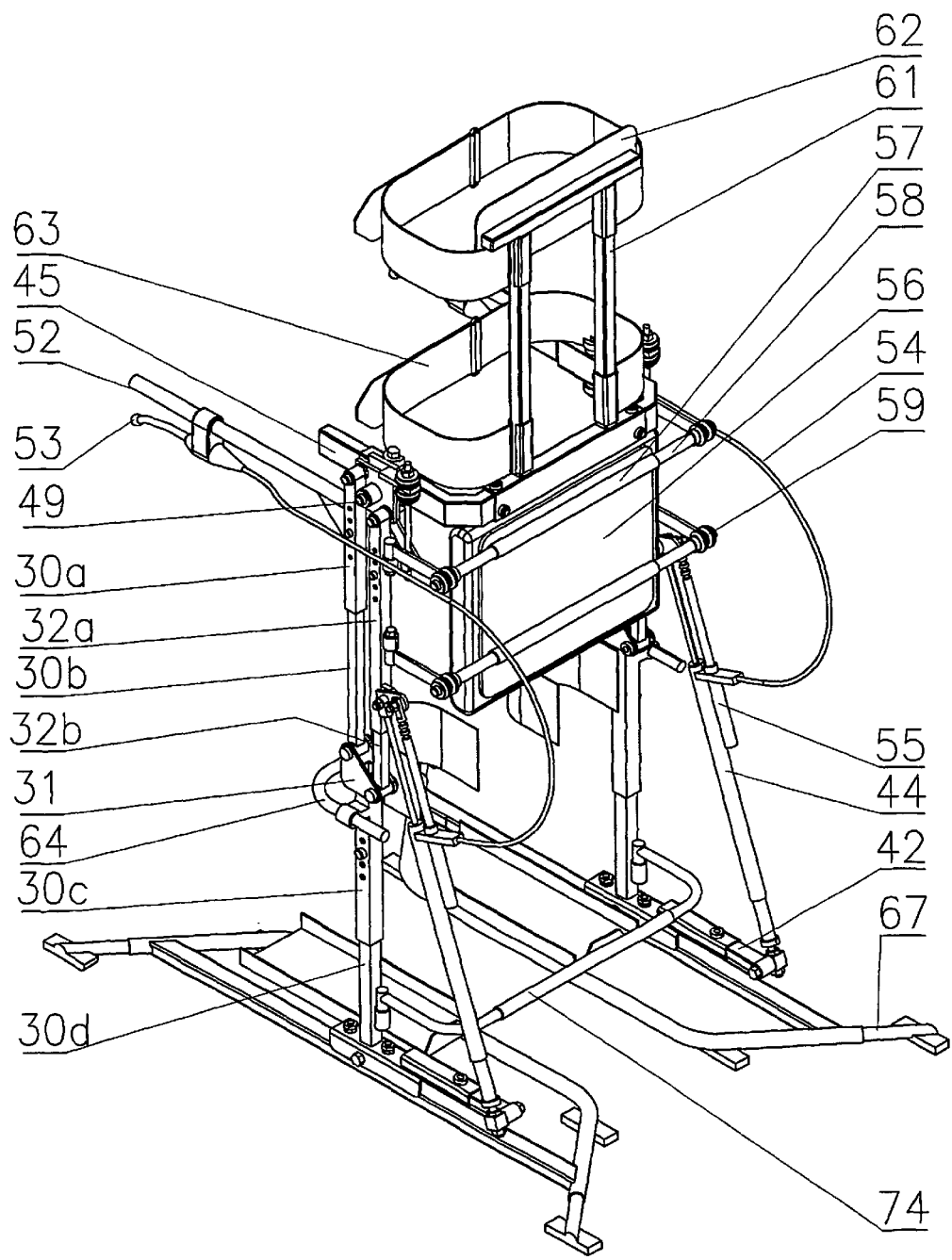
FIG. 7 is a perspective view of the device, seeing from the rear.
Figure 8:
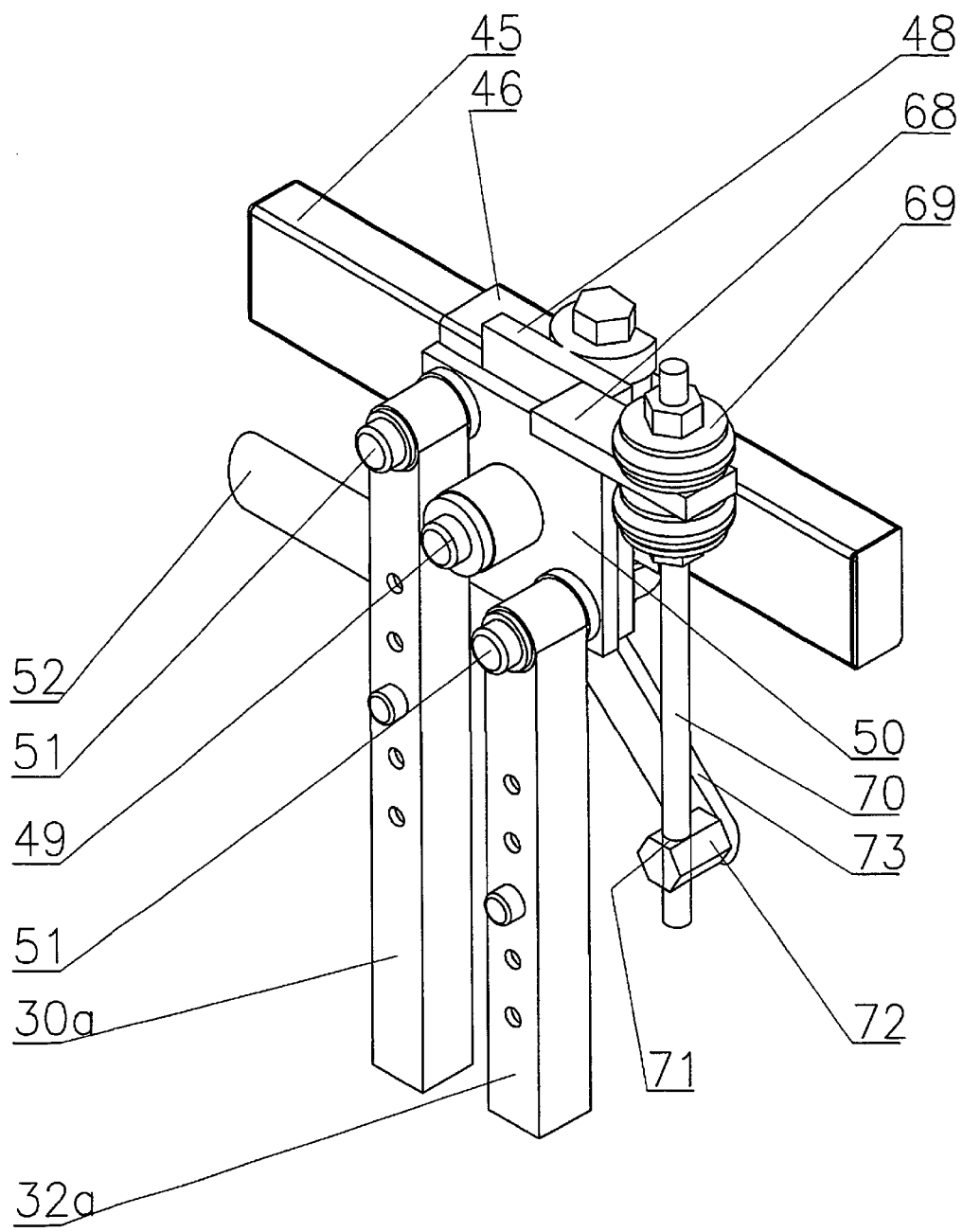
FIG. 8 is a perspective view of the junction of channel bar grip and the square plate seeing from the rear.
Figure 9:
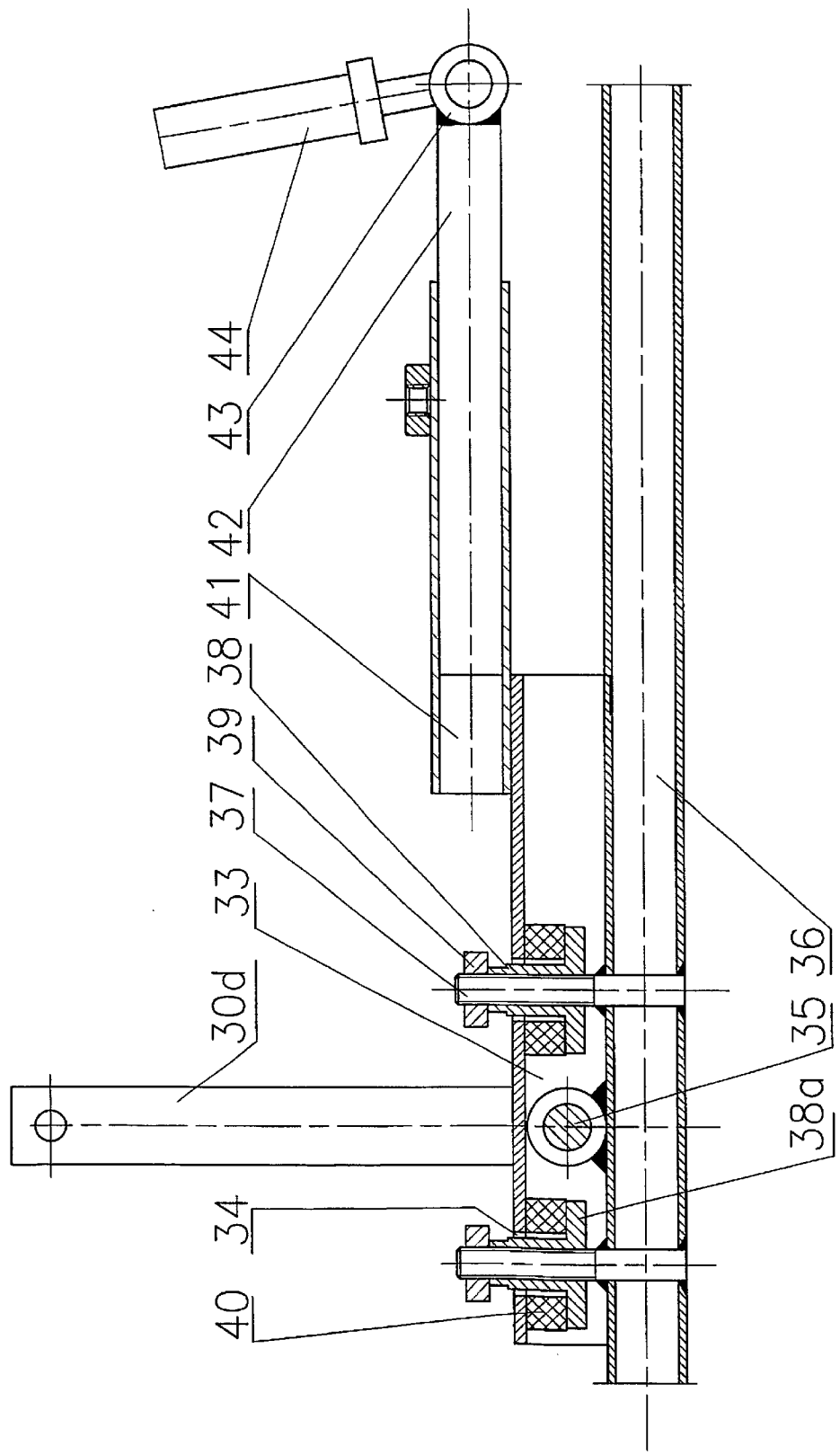
FIG. 9 is a view of portion of foot element with section of channel bar, with a bracket and sliding bar shown in longitudinal section.
Figure 10:
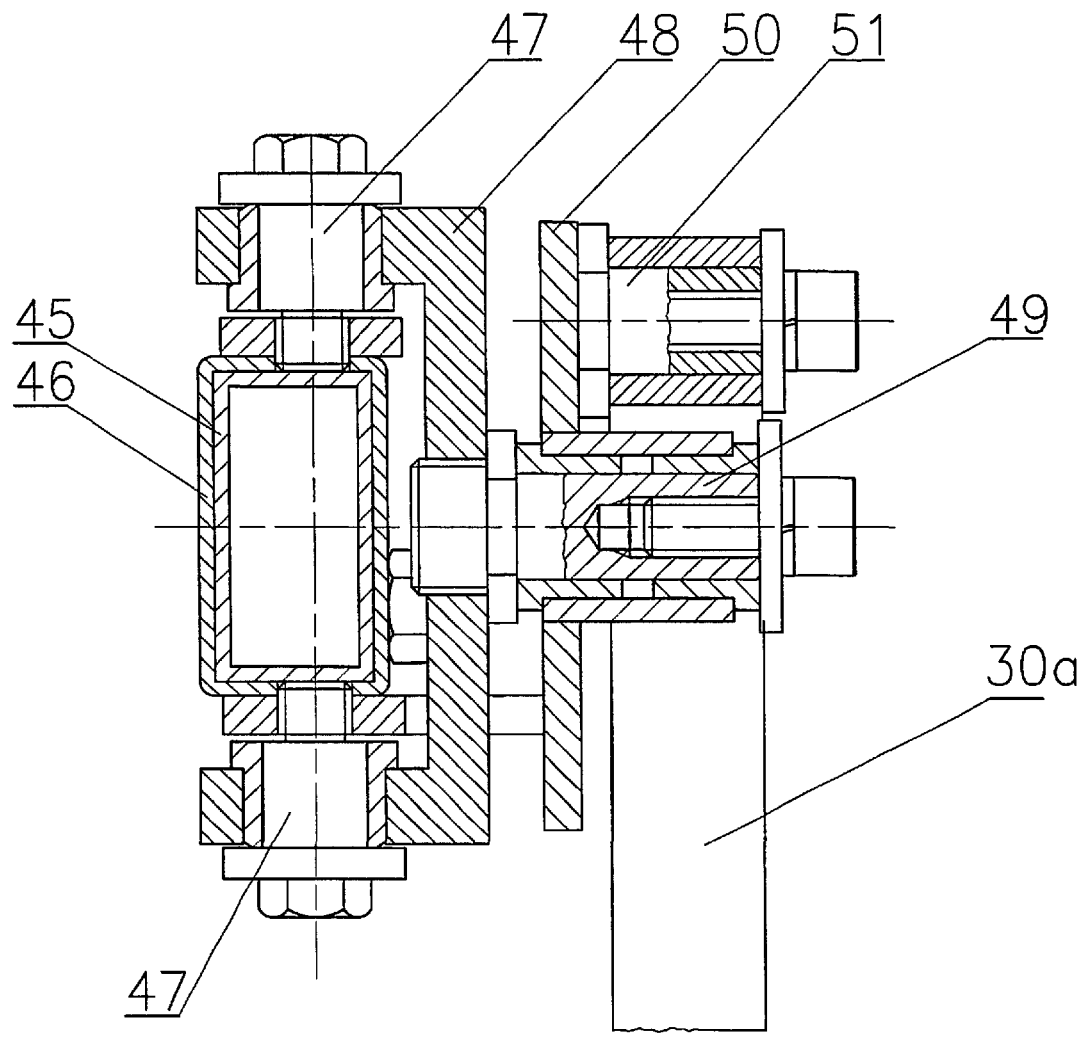
FIG. 10 is a view of jacket frame with sliding claps and channel bar grip and with square plate with bolt, shown in cross section.
Figure 11:
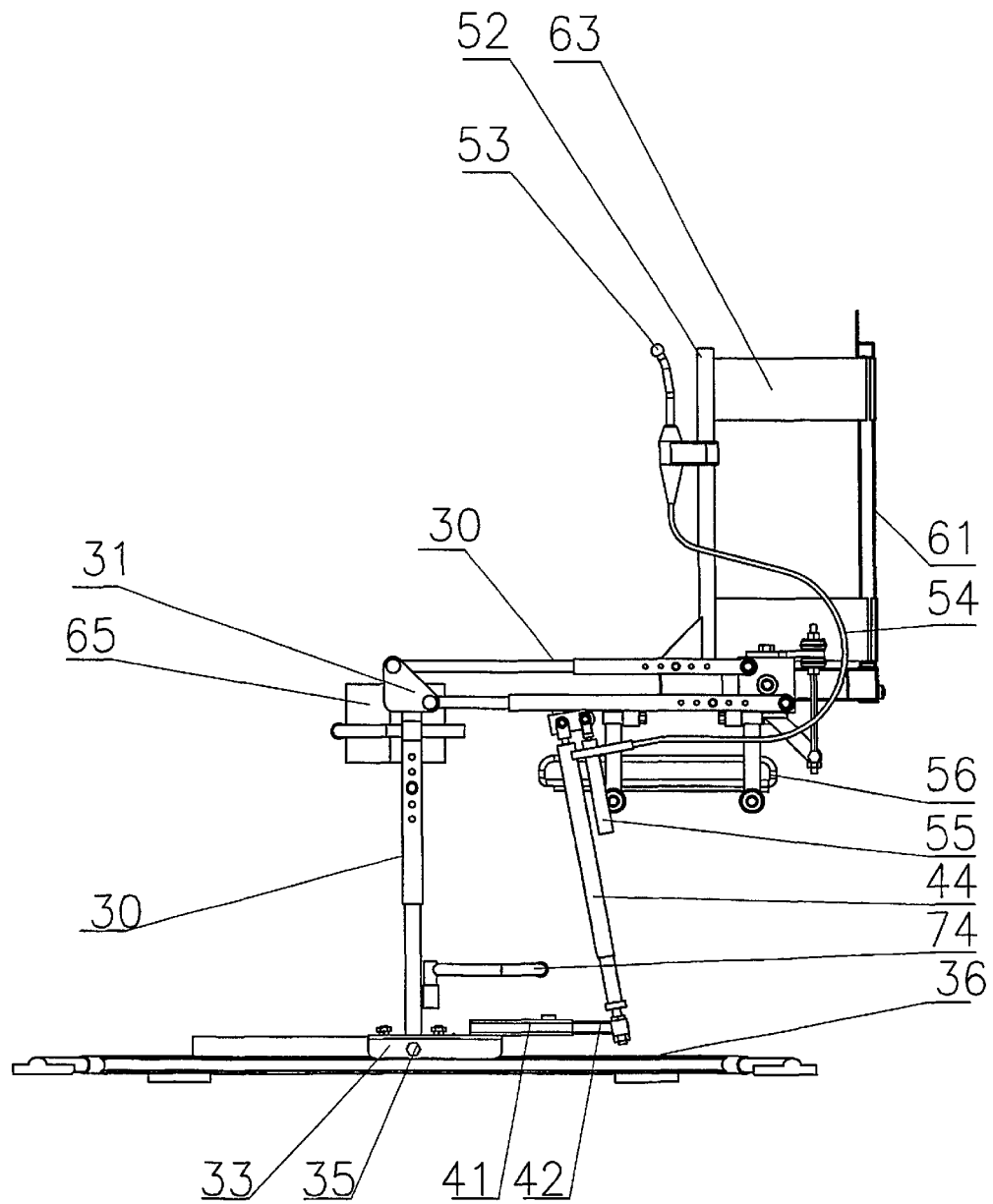

And FIG. 11 is a perspective lateral view of the device in its seated position.

The rehabilitation device for persons with paresis of lower limbs enabling them to walk comprises two basic rocking elements 1 consisting of two pairs of members: upper pair of members 2 and 3 and lower pair of members 4 and 5, where members 3 and 4 are interconnected pivotally, and comprises, two auxiliary rocking elements 6, parallel to upper pair of members 2 and 3 of basic rocking elements, each auxiliary rocking element consisting of one pair of members 7 and 8. Members 3b of auxiliary rocking elements 3 are also pivotally connected to connectors 9. fixed to members 4 of basic rocking elements 1. The members 5 of basic rocking elements 1 are pivotally connected to foot elements 10, and, at the upper part, the members 2 of basic rocking elements 1 and members 7 of auxiliary rocking elements 6 are pivotally connected to angular connectors 11 having bolts 12 fixed rotatably in claps 13 slidably mounted on the jacket frame 14. To the foot elements 10, at a distance from pivot joints mounting members 5 of basic elements 1, are pivotally attached spring, pneumatic or hydraulic shock absorbers 15 or pneumatic or hydraulic cylinders acting as servomotors, of whose pistons 16 are mounted pivotally to members 8 of auxiliary rocking elements 6. The foot elements 10 are trapezoidal in shape, whose arms 17 have supports 18, which can be extended outwardly, and brackets 19 at their ends, while to the longer sides 20 are pivotally mounted members 5 of basic rocking elements 1 as well as spring, pneumatic or hydraulic shock absorbers or servomotors 15 and, to the shorter sides 21 of trapezoidal foot elements 10 are mounted foot platforms 22. Underneath shorter sides 21 of trapezoidal foot elements 10, just under foot platforms 22 are fastened flexible pads 23, and under brackets 19 are fastened flexible pads 24, with height slightly less than that of pads 23. The auxiliary rocking elements 6 are interconnected, by means of bipartite shafts 25 to which is mounted plate 26. To the jacket frame 14, at its rear portion, are mounted bipartite jibs 27, with bipartite connecting rod 28 at their upper ends, and, in front part of the jacket frame 14 are mounted handles 29 for user's hands.

In another embodiment of the invention, the device comprises two basic rocking elements 30 consisting of two pairs of members: upper pair of members 30a and 30b and lower pair of members 30c and 30d, where members 30b and 30c are interconnected pivotally by means of connectors 31, and comprises, two auxiliary rocking elements 32, parallel to upper pair of members 30a and 30b of basic rocking elements 30, each auxiliary rocking element consisting of one pair of members 32a and 32b. Members 32b of auxiliary rocking elements 32 are also pivotally connected to connectors 31. The members 30d of basic rocking elements 30 are fixed, at their lower portion, so channel bar sections 33 with holes 34, which channel bar sections 33 are pivotally attached, by means of bolts 35 to middle part of longer side of trapezoidal foot elements 36. To the same longer side of trapezoidal foot elements 36 are solidly fixed, at either side of bolt 35, screw bolts 37 with threaded bushes 38 thereon, the latter having flanges 38a and being secured by clamp nuts 39, where the screw bolts 37 with bushes 38 pass through holes 34 in the channel bars sections 33, where the diameter of holes 34 is greater than the corresponding diameter of bushes 38. In the space between bottom surface of channel bar 33 and lower surface of the flange 38a of each bush 38 are situated rings 40, made of elastic material. Adjacent to ends opposite to bolts 35 of channel bars 33, are solidly attached brackets 41 with, each bracket 41 being equipped with a sliding arm 42, terminated by a solidly attached bush 43. Inside the bushes 43 are pivotally mounted ends of spring, or pneumatic or hydraulic shock absorbers 44, which, at their opposite ends, are pivotally attached to the members 32a f the auxiliary rocking elements 32. On the side arms of jacket frame 45, there are mounted sliding claps 46 with screw bolts 47, situated on the vertical axis of the sliding claps 46, onto which bolts 47 are mounted channel bar grips 48. To the front wall of each channel bar grip 48, is attached screwed bolt 49 having a square plate 50 pivotally mounted thereon. To the plates 50 are mounted, adjacent to its opposite corners, threaded bolts 51, to one of which is pivotally attached the end of member 30a of the basic rocking element 30, ant to the other bolt 51 is attached the end of member 32a of auxiliary rocking element 32. To the side of members 30a, of basic rocking elements 30, adjacent to their place of fixing on the threaded bolts 51 on the square plates 50, are mounted handles 52 for user's hands. On the ends of handles 52 are mounted levers 53 linked by means of flexible connectors 54 with locking mechanism 55, mounted on each spring or pneumatic or hydraulic shock absorber 44. Beneath of the jacket frame 45 a seat 56 is situated, to which are fastened underneath tubes 57, spaced apart, into which are slid-ably inserted two shafts 58 equipped at their respective ends with shock absorbers 59, made of elastic material, attached by means of additional rods 60 to members 32a of auxiliary rocking elements 32. Also, to the rear part of jacket frame 45 are fastened two jibs 61 with backrest 62 for the person's back, where said backrest 62 and jibs 61 are equipped with fastening belts 63. At the upper part of members 30c of basic rocking elements 30 are fastened jibs 64, bent at right angle, at the end of which are fastened slid ably and rotatable clasps 65 for supporting person's shins. To the front portions of trapezoidal foot elements 36 are fastened platforms 66 for person's feet. Besides, extending outwardly from the foot elements 36 there are slid able supports 67 with pads 67a at their ends. To the square plates 50, above, at the rear, is fastened a connector 68 with attached shock absorber 69 made from elastic material, with a screw rod 70 secured into a threaded hole 71 of a bolt 72, fixed pivotally in a connecting member 73, fixed solidly to the lower part of said bar grips 48. Additionaly to the lower part of the members 30d of the basic rocking elements 30 is fastened pivotally, at its respective ends, a stabilization shaft 74 which serves to assure parallel positions of basic rocking elements 1 during walking.

To use the device according to present invention, a handicapped person approaches the device on the wheel chair, the device being in its seated position, and the person is transferred onto device's seat 56, then the person puts his (her) feet on the foot platforms 66, puts shins into claps 65 and buckles fastening belts 63, then, unlocks locking mechanisms 55 by means of levers 53 and pushes down the handles 52 causing change of the seat position from seated to upright one, and at the same time causing standing position of the handicapped person.

The action of walking is carried out in such a way that the user, while holding the handles 52, performs swinging movements from left side to right side and at the same time pulling up alternately, left or right handle 23 causing forward strokes alternatively of left or right foot element 36

What is claimed is:

1. Rehabilitation device for persons with paresis of lower limbs enabling them to walk, comprising rocking elements having at their lower part foot elements with platforms for user's feet, said rocking elements being connected, at their upper part by a frame constituting a jacket, is characterized by the fact, that it has two basic rocking elements (1) and two auxiliary rocking elements (6), where the basic elements (1) consist of two pairs of members, the upper pair (2 and 3) and the lower pair of members (4 and 5), where the members of each pair are connected to each other by means of a pivot joint, while the auxiliary rocking elements (6) consist of one pair of members (7 and 8), each member of the pair connected at their lower portion by means of a pivot joint to connectors (9), which are connected to members (4) of basic rocking elements (1), which are connected, at their lower portion, to foot elements (10) with foot platforms (22), where, at the uppermost portion of basic rocking elements (1) and auxiliary rocking elements (6) are connected, by means of pivot joints to angular connectors (11) having bolts (12) rotatably mounted in clasps (13), slidably mounted on the jacket frame (14), and where the auxiliary rocking elements (6) are connected, at their lower portion to pistons of spring, gas or hydraulic shock absorbers or to pneumatic or hydraulic cylinders (15), acting as servomotors, which, at their other ends are pivotally connected to said foot elements (10), at a distance from connecting pivots of basic rocking elements (1).

2. Rehabilitation device according to claim 1, characterized by the fact, that said foot elements (10) consist each of a trapezoidal frame with two pairs of arms, the first pair of arms (20 and 21) being parallel to the axis of the person's movement, i.e. axis of symmetry of the device, and the second pair of arms (17) having supports (18) being able to extend outwardly in relation to the axis of symmetry of the device, and where the one, longer arm (20) of the first pair having pivotal joints for the basic rocking elements (1) and shock absorbers (15), and the second, shorter arm (21) having a foot platform (22) secured thereto.

3. Rehabilitation device according to claim 2, characterized by the fact, that said foot elements (10) each, having flexible pads (23 and 24) underneath, situated, one (23) just under the foot platform (22) and the two other (24) at the ends of outwardly extending supports (18) and where the latter pads (24) being slightly lower than the former one (23).

4. Rehabilitation device according to claim 1, characterized by the fact, that said auxiliary rocking elements (6) are interconnected by means of horizontal bipartite interconnections (25), to which is fixed a plate (26) constituting a seat.

5. Rehabilitation device for persons with paresis of lower limbs enabling them to walk, comprising rocking elements having at their lower part foot elements with platforms for user's feet, said rocking elements being connected, at their upper part by a frame constituting a jacket, is characterized by he fact, that the auxiliary members (30d) of basic rocking elements (30) are fixed, at their lower portion, to channel bar sections (33) with holes (34), which channel bar sections (33) are pivotally attached, by means of bolts (35) to middle part of longer side of trapezoidal foot elements (36) to which are solidly fixed, at either side of bolt (35), screw bolts (37) with threaded bushes (38) thereon, having flanges (38a) and being secured by clamp nuts (39), where the screw bolts (37) with bushes (38) pass through holes (34) in the channel bars sections (33), where the diameter of holes (34) is greater than the corresponding diameter of bushes (38). and in the space between bottom surface of channel bar (33) and lower surface of the flange (38a) of each bush (38) are situated rings (40), made of elastic material.

6. Rehabilitation device according to claim 5 characterized by the fact, that on the side arms of jacket frame (45), there are mounted sliding claps (46) with screw bolts (47), situated on the vertical axis of the sliding claps (46), onto which bolts (47) are mounted channel bar grips (48) with attached screwed bolt (49) having a square plate (50) pivotally mounted thereon, to which are mounted, adjacent to its opposite corners, threaded bolts (51), to one of which is pivotally attached the end of member (30a) of the basic rocking element (30), ant to the other bolt (51) is attached the end of member (32a) of auxiliary rocking element (32), and, to the side of members (30a), of basic rocking elements (30), adjacent to their adjacent to their upper portion, are mounted handles (52) with levers (53) linked by means of flexible connectors (54) with locking mechanisms (55), mounted on each spring or pneumatic or hydraulic shock absorber (44).

7. Rehabilitation device according to claim 6, characterized by the fact, that to the square plates (50), is fastened from above, at its rear a connector (68) with attached shock absorber (69) made from elastic material, with a screw rod (70) secured in a threaded hole (71) of a bolt (72), fixed pivotally in a connecting member (73), fixed solidly to the lower part of said bar grips (48).

8. Rehabilitation device according to claim 5, characterized by the fact, that underneath seat (56) are fastened tubes (57), spaced apart, into which are slid-ably inserted two shafts (58) equipped at their respective ends with shock absorbers (59), made of elastic material, attached by means of additional rods (60) to members (32a) of auxiliary rocking elements (32).

* * * * *

UNITED STATES PATENT AND TRADEMARK OFFICE
CERTIFICATE OF CORRECTION

PATENT NO. : 6,770,040 B2
DATED : August 3, 2004
INVENTOR(S) : Perner et al.

It is certified that error appears in the above-identified patent and that said Letters Patent is hereby corrected as shown below:

<u>Title page,</u>
Insert Item
-- [73] Assignee: Firma Ortopedyczna "Medort" S.A., Warszawa (PL) --

Signed and Sealed this

Seventh Day of June, 2005

JON W. DUDAS
*Director of the United States Patent and Trademark Office*